United States Patent
Nagasawa

(10) Patent No.: US 6,635,455 B1
(45) Date of Patent: Oct. 21, 2003

(54) PROCESS FOR PRODUCING PYRROLE-2-CARBOXYLIC ACID

(75) Inventor: Toru Nagasawa, Gifu (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/868,895

(22) PCT Filed: Dec. 28, 1999

(86) PCT No.: PCT/JP99/07423

§ 371 (c)(1), (2), (4) Date: Jul. 5, 2001

(87) PCT Pub. No.: WO00/40743

PCT Pub. Date: Jul. 13, 2000

(30) Foreign Application Priority Data

Jan. 5, 1999 (JP) .................................................. 11/539

(51) Int. Cl.$^7$ ................................................ C01P 17/10
(52) U.S. Cl. ........................ 435/117; 435/121; 435/136; 435/280; 435/170
(58) Field of Search ................................ 435/117, 121, 435/136, 280, 170

(56) References Cited

FOREIGN PATENT DOCUMENTS

JP 6-98767 4/1994

OTHER PUBLICATIONS

Toru Nagasawa, et al., (Bioscience and Industry(Baiosaiensu to Indasutori), vol. 57, No. 6, pp. 395–396, "Carbon Dioxide Fixation by Reversible Decarboxylases", Jun. 1999.

Marco Wieser, et al., Tetrahedron Letters, vol. 39, No. 24, pp. 4309–4310, "Microbial Synthesis of Pyrrole–2–Carboxylate by Bacillus Megaterium PYR2910", Jun. 11, 1998.

Hironori Omura, et al., Eur. J. Biochem, vol. 253, No. 2, pp. 480–484, "Pyrrole–2–Carboxylate Decarboxylase from Bacillus Megaterium PYR2910, An Organic–Acid–Requiring Enzyme", 1998.

Toyokazu Yoshida, et al., Bio Industry, vol. 15, No. 12, pp. 44–49, "Microbial Regiospecific Hydroxylation and Carboxylation of N–Heterocyclic Compounds", 1998.

T. B. Kazanskaya, et al., Mikrobiologiya, vol. 50, No. 6, XP–002188170, pp. 992–995, "Decarboxylase Activity of Serratia–Marcescens Strains Utilizing Glucose and Glycerol" Jun., 1981 (with English Abstract (1page) and English Translation (pp. 740–742).

*Primary Examiner*—Irene Marx
(74) *Attorney, Agent, or Firm*—Oblon, Spivak, McClelland, Maier & Neustadt, P.C.

(57) ABSTRACT

A process for producing pyrrole-2-carboxylic acid which comprises the steps of:

allowing a microorganism that is derived from the genus Serratia, is capable of catalyzing decarboxylation of pyrrole-2-carboxylic acid, and is capable of catalyzing the synthesis of pyrrole-2-carboxylic acid from pyrrole in the presence of carbonate ion, or the microorganism optionally processed, to act on pyrrole; and recovering the pyrrole-2-carboxylic acid generated.

23 Claims, No Drawings

PROCESS FOR PRODUCING PYRROLE-2-CARBOXYLIC ACID

FIELD OF THE INVENTION

The present invention relates to a novel process for producing pyrrole-2-carboxylic acid from pyrrole by action of microorganisms. Pyrrole-2-carboxylic acid and its derivatives are useful as raw materials for various drugs.

BACKGROUND ART

In vivo enzymatic decarboxylation for amino acids and α-keto acids has been studied well, so that the properties of enzymes involved in the reaction is now clearly understood. However, much remains unclear regarding nonoxidative decarboxylase for aromatic carboxylic acids.

A known nonoxidative decarboxylating reaction of aromatic carboxylic acid by a microorganism is A reaction to convert a hydroxybenzoic acid into phenol (Microb. Ecol., 20, 103, 1990). Moreover, bacteria belonging to the genus Citrobacter are known to decarboxylate a gallic acid so as to generate and accumulate pyrogallol (Agric. Biol. Chem., 46, 2539, 1982).

On the other hand, a microorganism known to catalyze carbon dioxide fixation to aromatic compounds is a bacterium belonging to the genus Pseudomonas that converts phenol to 4-hydroxybenzoic acid in the first step towards decomposition of phenol (Arch. Microbiol., 148, 213, 1987).

Furthermore, properties of an enzyme derived from the genus Clostridium have been examined in detail. That is, the enzyme has been shown to catalyze decarboxylation and carbon dioxide fixation of 4-hydroxybenzoic acid and of 3,4-dihydroxybenzoic acid by a reversible reaction (Appl. Environ. Microbiol., 60, 4182, 1994).

Industrial application of the synthesis of carboxylic acid by carbon dioxide fixation to aromatic compounds has great value. However, carbon dioxide-fixing activity of the above-mentioned microorganisms and enzyme is so poor that they cannot easily be practically applied.

As a result of thorough studies on enzymes which catalyze carbon dioxide fixation to aromatic compounds, we have previously found that pyrrole-2-carboxylic acid decarboxylase derived from the genus Bacillus performs carbon dioxide fixation to pyrrole, so as to synthesize pyrrole-2-carboxylic acid (Eur. J. Biochem., 253, 480, 1998).

However, the reaction system of this enzyme requires the co-existence of an organic acid, such as ammonium acetate. This is inconvenient when considering, for example, the isolation of products.

SUMMARY OF THE INVENTION

Under the circumstances, we have completed the present invention as a result of devoted study, by finding that microorganisms, which are derived from bacteria belonging to the genus Serratia and decarboxylate pyrrole-2-carboxylic acid, stably perform the reaction in the absence of organic acid ammonium.

That is, the present invention provides a process for producing pyrrole-2-carboxylic acid comprising the steps of allowing a microorganism, which is derived from the genus Serratia, is capable of catalyzing decarboxylation of pyrrole-2-carboxylic acid, and is capable of catalyzing the synthesis of pyrrole-2-carboxylic acid from pyrrole in the presence of carbonate ion, or the microorganism optionally processed, to act on pyrrole; and recovering the pyrrole-2-carboxylic acid which is generated.

Further, the present invention provides the above process for producing pyrrole-2-carboxylic acid wherein the microorganism or the microorganism optionally processed is allowed to act in the absence of organic acid.

Furthermore, the present invention provides an enzyme which is extracted from a microorganism belonging to the genus Serratia, is capable of catalyzing decarboxylation of pyrrole-2-carboxylic acid, and is capable of catalyzing the synthesis of pyrrole-2-carboxylic acid from pyrrole in the presence of carbonate ion.

The present invention also provides the above described enzyme wherein the microorganism belonging to the genus Serratia is *Serratia grimesii* (IFO13537), *Serratia marcescens* (IAM12142), or *Serratia rubidaea* (IFO12973).

This specification includes part or all of the contents as disclosed in the specification and/or drawings of Japanese Patent Application No. 11-539, which is a priority document of the present application.

Now a detailed description of this invention will be given.

BEST MODE FOR CARRYING-OUT OF THE INVENTION

A microorganism of the present invention is derived from the genus Serratia, catalyzes decarboxylation of pyrrole-2-carboxylic acid, and has activity to convert pyrrole to pyrrole-2-carboxylic acid in the presence of carbonate ion. Examples of such a strain include *Serratia grimesii* (IFO13537), *Serratia marcescens* (IAM12142), and *Serratia rubidaea* (IFO12973).

These microorganisms are known. Strains IFO13537 and IFO12973 are easily obtained from the Institute for Fermentation, 17-85, Juso-honmachi, 2-chome, Yodogawa-ku, Osaka 532-8686, Japan, and IAM12142 from the Institute of Molecular and Cellular Biosciences (IAM), University of Tokyo, 1-1-1 Yayoi, Bunkyo-ku, Tokyo 113, Japan, respectively.

Generally, a medium for culturing microorganisms in the present invention may be any one in/on which they can grow. Examples of carbon sources include sugars, such as glucose, sucrose, and maltose; organic acids, such as acetic acid, citric acid and fumaric acid, or salts thereof; and alcohols, such as ethanol and glycerol. Examples of nitrogen sources include general and natural nitrogen sources, such as peptone, meat extract, yeast extract, and amino acid, and various inorganic and organic acid ammonium salts and the like. If necessary, inorganic salts, trace mineral salts, vitamins and the like are added appropriately. Moreover, addition to a medium of pyrrole-2-carboxylic acid, benzoic acid, anthranilic acid and their derivatives and the like as inducers for enzyme production is effective to obtain high enzymatic activity.

Culturing may be performed by standard techniques. For example, culturing is performed at pH 4 to 10, and at a temperature ranging from 15° C. to 40° C. aerobically for 6 to 96 hours.

The reaction for producing pyrrole-2-carboxylic acid can be performed by allowing the microorganisms above or those optionally processed to contact with pyrrole in the presence of carbonate ion and in water or in a buffer such as phosphoric acid buffer, carbonic acid buffer, boric acid buffer and the like.

Examples of an optionally processed microorganism include, but are not limited to, a culture product from the microorganisms, viable cells, dried cells, disrupted cells, enzyme extract solution, and crude/purified enzyme.

Reaction may be performed generally at pH ranging from 4 to 10, preferably pH 5 to 9, and at a temperature ranging from 0 to 60° C., preferably 5 to 50° C. Suitable concentration of pyrrole varies depending on reaction temperature and pH. Generally, a preferable concentration of pyrrole ranges from 50 to 300 mM. In addition, the amount of microorganisms or that of those optionally processed to be used generally ranges from 0.01 to 5 wt % on a conversion with dried cell relative to a substrate.

Examples of the sources of carbonate ion include carbonates, such as sodium, potassium, and ammonium carbonates, of which ammonium bicarbonate, sodium bicarbonate and the like are particularly effective. Since this reaction is an equilibrium reaction, reaction yield can be further increased by performing the reaction under carbon dioxide gas pressure in addition to the presence of these salts.

Pyrrole-2-carboxylic acid can be recovered from the reaction solution by known methods including bacteria elimination, concentration, anion exchange chromatography, and crystallization.

EXAMPLES

The present invention will be described below by use of Examples.

Reference 1

A 30 ml of medium (pH 7.0) consisting of 10 g/l sodium fumarate, 10 g/l polypeptone, 1.5 g/l pyrrole-2-carboxylic acid (or 3.0 g/l pyrrole-2-carboaldehyde), 0.5 g/l yeast extract, 0.5 g/l $MgSO_4 \cdot 7H_2O$, 1 g/l $K_2HPO_4$ and 5 ml/l metal salt mixture was dispensed into 500 ml Sakaguchi flasks, and then heated for sterilization at 121° C. for 15 min. Then, strains as shown in Table 1 were inoculated, followed by shake culturing at 28° C. for 24 hours.

Here, the metal salt mixture (solution) consisted of 300 mg/l $H_3BO_4$, 400 mg/l $CaCl_2 \cdot 2H_2O$, 40 mg/l $CuSO_4 \cdot 5H_2O$, 100 mg/l KI, 200 mg/l $FeSO_4 \cdot 7H_2O$, 400 mg/l $MnSO_4 \cdot 7H_2O$, 200 mg/l $H_2MoO_4 \cdot 2H_2O$, and 10 ml/l concentrated hydrochloric acid.

After culturing, cells were collected by centrifugation (10,000×g, 15 min.), and then washed with 0.85% NaCl solution, the volume of which was the same as that of the culture solution. Cells were then suspended in 1.5 ml of the 0.85% NaCl solution [$OD_{610}$=9.0 (dry weight of the cells: about 4.5 mg/ml)].

The above cell suspension 0.5 ml was added to a reaction solution consisting of 0.5 ml (200 μmol) of 0.4 M pyrrole-2-carboxylic acid solution, and 1 ml of 0.4 M potassium phosphate buffer (pH 7.0). Next, the mixture was shaken at 30° C. for 10 minutes, and then the reaction was stopped by adding 0.5 ml of 0.5N NaOH solution. The reaction solution was centrifuged (10,000×g, 15 min.) for bacteria elimination. The resulting supernatant was subjected to high performance liquid chromatography (Shimadzu 3PD-10A, Shimadzu Corp., The column was Spherisorb S-500S2 (15×160 mm)). Pyrrole was quantified with absorption at 210 nm.

The results are shown in Table 1.

| Strain | Pyrrole generated (μmol) |
|---|---|
| Serratia grimesii IFO 13537 | 8.46 |
| Serratia marcescens IAM 12142 | 1.46 |
| Serratia rubidaea IFO 12973 | 0.175 |

Example 1

Serratia grimesii IFO 13537 was cultured and washed in the same manner as in Reference 1. Then, the cells were suspended in 0.1M potassium phosphate buffer (pH7.0) containing 1 mM dithiothreitol so that the cells were concentrated 15-fold for the culture solution ($OD_{610}$=9.0 (about 4.5 mg/ml dried cells)). Subsequently, the cells were disrupted with a sonicator (Kubota INSONATOR 201M). The resulting solution was centrifuged (10,000×g, 15 min.) to obtain a supernatant, and then a 40 to 70% saturated ammonium sulfate fraction was obtained by standard techniques. The fraction was dialyzed with 20 mM potassium phosphate buffer (pH 7.0) to obtain crude enzyme solution.

The above crude enzyme solution 0.2 ml was added to a reaction solution (about 2 ml) consisting of 0.03 ml of 200 mM pyrrole, 0.2 ml of 1M potassium phosphate buffer (pH 6.0), 0.6 g of $KHCO_3$, 0.2 ml of 0.2M dithiothreitol solution, and 1.386 ml of distilled water, and then allowed to react at 30° C. for 3 hours.

The reaction solution was subjected to high performance liquid chromatography (Shimadzu SPD-10A) with a Spherisorb S-50DS2 (15×60 mm) column and a solvent system [10mM $KH_2PO_4$—$H_3PO_4$ (pH 2.5):$CH_3CN$=8:2(v/v)]. Then, absorbance at 210 nm was detected so that pyrrole and pyrrole-2-carboxylic acid were quantified. As a result, generation of 140 mM pyrrole-2-carboxylic acid (yield: about 70%) was confirmed.

Example 2

Serratia grimesii IFO 13537 was cultured and washed in the same manner as in Reference 1, and then a solution containing the disrupted cells was prepared in the same manner as in Example 1. This solution was centrifuged (10,000 g, 15 min.) so as to obtain a supernatant. Then, a 40 to 60% saturated ammonium sulfate fraction was obtained by standard techniques. The fraction was dialyzed with 20 mM potassium phosphate buffer containing 100 mM acetic acid and 1 mM DTT, followed by another dialysis with 50% glycerol containing 1 mM DTT, thereby obtaining a crude enzyme solution.

Two groups, each of which included three types of samples with 200, 225, and 250 mM respectively, of starting concentrations of pyrrole were set. 1M potassium phosphate buffer (pH 5.5) 0.1 ml, 0.3 g of $KHCO_3$, 0.1 ml of 0.2M dithiothreitol solution, 0.4 ml of crude enzyme solution were added to each of these samples, and then allowed to react for 3 hours.

One group was fed with 100 mM pyrrole 3 hours later, while the other group was not fed. The two groups were then allowed to react for another 9 hours. Then, the amount of pyrrole-2-carboxylic acid generated was quantified. Table 2 shows the results.

TABLE 2

| Condition | | Pyrrole-2-carboxylic acid |
|---|---|---|
| Pyrrole | Feed | (mM) |
| 200 mM | No feed | 140 |
| | Feed | 210 |
| 225 mM | No feed | 145 |
| | Feed | 225 |
| 250 mM | No feed | 155 |
| | Feed | 230 |

As shown in Table 2, the higher the starting concentration of pyrrole, the greater amount of pyrrole-2-carboxylic acid obtained. Moreover, addition of pyrrole as a reaction substrate resulted in a further increase in the amount generated.

Example 3

*Serratia grimesii* was cultured in the same manner as in Reference 1, thereby preparing the cell suspension. Pyrrole 400 mM, 0.1 ml of 1M potassium phosphate buffer (pH 5.5), 0.3 g of $KHCO_3$, 0.1 ml of 0.2M dithiothreitol solution, and 28 g of dried cells were added to the suspension, and then shaken at 20° C. for 12 hours. Subsequently, 0.25 ml of 0.5N NaOH solution was added to the mixture to stop reaction. Thus, the pyrrole-2-carboxylic acid generated was quantified.

On the other hand, the suspension was treated in the same manner as described above except the use of 300 mM pyrrole, shaken for 2.5 hours, fed with 200 mM pyrrole, and then allowed to react for another 9.5 hours.

Table 3 shows the amount of pyrrole-2-carboxylic acid accumulated in each reaction.

TABLE 3

The amount of pyrrole-2-carboxylic acid accumulated in the reaction of the cells

| Condition | | Pyrrole-2-carboxylic acid (mM) | Conversion rate (%) |
|---|---|---|---|
| Starting concentration of pyrrole No feed | 400 mM | 278 | 71 |
| Starting concentration of pyrrole Feed* | 300 mM | 360 | 72 |

*Fed 2.5 hours after the start of reaction.

Example 4

An experiment was performed in the same manner as in Example 1 except that the cell used was *Serratia marcescens* (IAM 12142) or *Serratia rubidaea* (IFO 12973). As a result, generation of pyrrole-2-carboxylic acid was confirmed for the two strains.

INDUSTRIAL APPLICABILITY

In the present invention, isolation of the product from the microorganism is facilitated because the microorganism used herein possesses high ability in carbon dioxide fixation compared to standard microorganisms, and it does not require the co-existence of organic acid ammonium in its reaction system.

All publications, patents, and patent applications cited in this specification are incorporated herein by reference in their entirety.

What is claimed is:

1. A process for producing pyrrole-2-carboxylic acid comprising:

contacting a microorganism from the genus Serratia or a processed microorganism from the genus Serratia with pyrrole in the presence of carbonate ion for a time and under conditions which produce pyrrole-2-carboxylic acid, and recovering pyrrole-2-carboxylic acid;

wherein said microorganism catalyzes the synthesis of pyrrole-2-carboxylic acid from pyrrole in the presence of carbonate ion.

2. The process of claim 1 comprising contacting a viable microorganism of the genus Serratia with pyrrole.

3. The process of claim 1 comprising contacting pyrrole with a processed microorganism of the genus Serratia, wherein said processed microorganism comprises dried cells of a microorganism of the genus Serratia.

4. The process of claim 1 comprising contacting pyrrole with a processed microorganism of the genus Serratia, wherein said processed microorganism comprises disrupted cells of a microorganism of the genus Serratia.

5. The process of claim 1 comprising contacting pyrrole with a processed microorganism of the genus Serratia, wherein said processed microorganism comprises an enzyme extract solution of a microorganism of the genus Serratia.

6. The process of claim 1 comprising contacting pyrrole with a processed microorganism of the genus Serratia, wherein said processed microorganism comprises a crude enzyme solution of a microorganism of the genus Serratia.

7. The process of claim 1, wherein said microorganism or processed microorganism is contacted with pyrrole in a buffer comprising phosphoric acid, carbonic acid or boric acid.

8. The process of claim 1, wherein said microorganism or processed microorganism is contacted with pyrrole at a pH ranging from 4 to 10.

9. The process of claim 1, wherein said microorganism or processed microorganism is contacted with pyrrole at a pH ranging from 5 to 9.

10. The process of claim 1, wherein said microorganism or processed microorganism is contacted with pyrrole at a temperature ranging from 0 to 60° C.

11. The process of claim 1, wherein said microorganism or processed microorganism is contacted with pyrrole at a temperature ranging from 5 to 50° C.

12. The process of claim 1, wherein said microorganism or processed microorganism is contacted with pyrrole at a temperature ranging from 15 to 40° C.

13. The process of claim 1, wherein said microorganism or processed microorganism is *Serratia marcescens*.

14. The process of claim 1, wherein said microorganism or processed microorganism is *Serratia grimesii*.

15. The process of claim 1, wherein said microorganism or processed microorganism is *Serratia rubidaea*.

16. The process of claim 1, wherein the source of said carbonate ion is sodium carbonate.

17. The process of claim 1, wherein the source of said carbonate ion is potassium carbonate.

18. The process of claim 1, wherein the source of said carbonate ion is ammonium carbonate.

19. The process of claim 1, further comprising contacting said microorganism or processed microorganism with pyrrole in the presence of benzoic acid or anthranilic acid.

20. The process of claim 1, wherein said microorganism or processed microorganism is, or is obtained from, *Serratia marcescens* (IAM12142).

21. The process of claim 1, wherein said microorganism or processed microorganism is, or is obtained from, *Serratia grimesii* (IFO13537).

22. The process of claim 1, wherein said microorganism or processed microorganism is, or is obtained from, *Serratia rubidaea* (IFO12973).

23. The process of claim 1, which is conducted under pressure in the presence of carbon dioxide.

* * * * *